(12) United States Patent
Bondarev

(10) Patent No.: US 7,741,296 B2
(45) Date of Patent: Jun. 22, 2010

(54) MODULATION OF TELOMERE LENGTH IN TELOMERASE POSITIVE CELLS AND CANCER THERAPY

(76) Inventor: Igor E. Bondarev, 25-1-123 Solidarnosty Pr., St. Petersburg, 193231 (RU)

( * ) Notice: Subject to any disclaimer, the term of this patent is extended or adjusted under 35 U.S.C. 154(b) by 214 days.

(21) Appl. No.: 11/886,446

(22) PCT Filed: Mar. 27, 2006

(86) PCT No.: PCT/US2006/011027
§ 371 (c)(1), (2), (4) Date: Sep. 13, 2007

(87) PCT Pub. No.: WO2006/104975
PCT Pub. Date: Oct. 5, 2006

(65) Prior Publication Data
US 2009/0023677 A1    Jan. 22, 2009

Related U.S. Application Data

(60) Provisional application No. 60/665,105, filed on Mar. 25, 2005.

(51) Int. Cl.
*A01N 43/04* (2006.01)
*A61K 31/70* (2006.01)
(52) U.S. Cl. .............................. 514/43; 514/45; 514/46; 514/49; 514/50
(58) Field of Classification Search .................. None
See application file for complete search history.

(56) References Cited

U.S. PATENT DOCUMENTS 5,166,140 A * 11/1992 Scanlon et al. ................ 514/45

* cited by examiner

*Primary Examiner*—Patrick T Lewis
(74) *Attorney, Agent, or Firm*—Stites & Harbison PLLC; Juan Carlos A. Marquez, Esq.

(57) ABSTRACT

Induction of telomere shortening, G2 arrest and apoptosis in telomerase positive cancer cells using acyclic nucleoside analogs has been disclosed. In addition, methods for impairment or prevention of tumorigenic telomerase positive cells from having a chance to grow into a tumor and methods for promoting tumor regression (decrease in size of an established tumor) using acyclic nucleoside analogs has been disclosed.

20 Claims, 3 Drawing Sheets

MODULATION OF TELOMERE LENGTH IN TELOMERASE POSITIVE CELLS AND CANCER THERAPY

This application claims the benefit of U.S. Provisional Application No. 60/665,105 filed Mar. 25, 2005, and the disclosure of application 60/665,105 is incorporated by reference in its entirety herewith.

FIELD OF THE INVENTION

The present invention is directed to the field of cancer therapy. Specifically, the present invention relates to the regulation of telomere elongation in telomerase positive cells. More particularly, the present invention relates to the use of acyclic nucleoside analogs including ganciclovir (GCV), acyclovir (ACV) and their ester pro-drugs for interfering with telomere elongation, for induction of apoptosis and for treating or preventing telomerase positive cancers.

BACKGROUND OF THE INVENTION

An asymmetry in the synthesis of leading and lagging DNA strands creates the "end problem" for replication of linear genomes.[1] To overcome this problem, eukaryotic chromosomes have specialized end structures, telomeres, consisting of TTAGGG repeats.[2] Telomerase[3,4] is a ribonucleoprotein enzyme that elongates telomeres and therefore maintains chromosomal stability in majority of cancer cells during cell doubling.[5] The gradual loss of DNA from the ends of telomeres during cell doubling has been implicated in the control of cellular proliferative potential in somatic cells.[6]

Normal cultured human cells have a limited replication potential in culture. Normal cells in culture replicate until they reach a discrete point at which population growth ceases. This is termed mortality stage 1 (M1 stage) and is caused by the shortening of a few telomeres to a size that leads to a growth arrest called cellular senescence. This stage can be bypassed by abrogation of the function of p53 and pRB human tumor suppressor genes. The cells then can continue to proliferate with further decreases in telomere length until another check point termed mortality stage 2 (M2 stage) or crisis stage. The growth arrest in the M2 stage is caused by balance between the cell proliferation and cell death rate. At this stage, when most of the telomeres are extremely short, end-to-end fusions and chromosomal breakage-fusion cause marked chromosomal abnormalities and apoptosis. Under rare circumstances, a cell can escape M2 and become immortal by stabilizing the length of its telomeres. This occurs through the activation of the enzyme telomerase or an alternative mechanism of telomere lengthening (ALT).[7,8]

Human germline[9] and the majority of cancer cells[3] express telomerase. Telomerase is a ribonucleoprotein enzyme that elongates telomeres and, therefore, maintains chromosomal stability in majority of cancer cells during cell doubling.[10] Indeed, elongation of shortened telomeres by telomerase is a major mechanism of telomere maintenance in the human cancer cells. Inhibition of telomerase limits the growth of human telomerase positive cancer cells[11] by decreasing telomere length.

Elongation of shortened telomeres by telomerase is a well known mechanism of telomere maintenance in the human cancer cells. From a biological point of view, telomerase elongates telomeres by the addition of repetitive DNA sequences of the TTAGGG-type (telomeric sequences), at the end of the telomere, during cell division. Through this action, telomerase imparts chromosomal stability and renders the cell immortal. In attempting to obtain selective inhibitors as useful tools for studying this enzyme, inhibitory effects of nucleotide analogues have been investigated in cell-free systems (Yamaguchi et al., (2001, Nucleic Acids Research Supplement No. 1 211-212). Since proliferating cells including cancer cells express telomerase activity while normal human somatic cells do not express telomerase activity at levels sufficient to maintain telomere length over many cell divisions as seen in cancer cells, telomerase is a good target for treating proliferative disorders including cancer.

Currently, strategies aimed at selectively treating the cancers from telomerase positive cells involve modulation of TERT (Telomerase Reverse Transcriptase) function or length of telomeres by antisense strategy, dominant negative mutants or pharmacological agents (see, Bisoffi et al., Eur J Cancer, 1998, 34: 1242-1249; Roth et al., Leukemia, 2003, 17:2410-2417; Damm et al., EMBO J., 2001, 20:6958-6968; U.S. Pat. Nos. 6,294,332, 6,194,206, 6,156,763 and 6,046, 307). The use of nucleoside analogs (e.g., AZT) has been attempted to interfere with human telomerase activity with an aim to treat cancers. The methods disclosed in the prior art administering nucleoside analogs to modify telomerase activity, however, are not satisfactory or are not suitable in a clinical setting because their clinical utility is limited by a low therapeutic ratio, i.e., the ratio of toxic dose to effective dose.

Prolonged exposure of telomerase positive cell lines to AZT failed to induce any significant telomere shortening at a concentration of the drug equal to 100 μM (Murakami, J., Nagai. N., Shigemasa. K., Ohama. K. Inhibition of telomerase activity and cell proliferation by a reverse transcriptase inhibitor in gynaecological cancer cell lines. *Eur. J. Cancer* 35, 1027-1034 (1999) or even 800 μM (Gomez D E, Tejera A M, Olivero O A. Irreversible telomere shortening by 3'-azido-2',3'-dideoxythymidine (AZT) treatment. *Biochem Biophys Res Commun.* 1998; 246(1): 107-10; Tejera A M, Alonso D F, Gomez D E, Olivero O A. Chronic in vitro exposure to 3'-azido-2',3'-dideoxythymidine induces senescence and apoptosis and reduces tumorigenicity of metastatic mouse mammary tumor cells. *Breast Cancer Res Treat.* 2001; 65(2): 93-9).

While peak serum concentration after taking single oral dose of 300 mg of AZT was less than 10 μM, and it was rapidly absorbed within 0.5 h (Morse G D, Olson J, Portnore A, Taylor C, Plank C, Reichman R C Pharmacokinetics of orally administered zidovudine among patients with hemophilia and asymptomatic human immunodeficiency virus (HIV) infection. *Antiviral Res.* 1989 March; 11(2):57-65). Standard AZT treatment is 500 or 600 mg/day in two or three divided doses for adults according to the recommendations of the manufacturer of Retrovir® (AZT). It has been reported that even a short-time exposure to AZT at a concentration of 5 μM induces undesirable toxic effects on mammalian cells in vitro and in vivo (Roskrow M, Wickramasinghe S N. Acute effects of 3'-azido-3'-deoxythymidine on the cell cycle of HL60 cells. *Clin Lab Haematol.* 1990; 12(2):177-84.). Based on these reports, one can predict that doses of nucleoside analogs such as AZT high enough to provide antitelomerase and antitumor efficacies can be highly toxic and cause damage to important tissues in humans. Thus, there is need for the identification of therapeutic nucleoside analogs, which have modulation or inhibitory activity against human telomerase, and development of methods of treatment of cancers in which telomerase contributes to the immortality and undesirable proliferation.

SUMMARY OF THE INVENTION

The present invention provides compositions containing antiviral nucleoside analogs and methods for their use in the modulation, suppression or inhibition of eukaryotic telomerase activity and treatment of proliferative disorders including cancer. More particularly, the present invention discloses that acyclic nucleoside analogs or those nucleoside analogs that are active as anti-herpesvirus and anti-cytomegolovirus agents can modify telomerase activity in proliferating cells including cancer cells and thus function as antineoplastic agents. In an aspect of the invention, it has been found that treatment of telomerase positive cells with ganciclovir or acyclovir induces progressive telomere loss, G2 phase arrest, chromosomal abnormalities and eventual cell death.

Further, these antineoplastic nucleoside analogs have a surprising effect on telomerase in that clinically acceptable levels are sufficient to control telomerase activity and induce cell death in proliferating cells. These findings now offer new avenues of therapy for treatment or prevention of cancers characterized by telomerase activity (telomerase positive cancers).

Currently, there are no therapeutic compositions in use that are based on nucleoside analogs that are acyclic, antitelomerase and antineoplastic. Applicant is the first to provide a disclosure indicating that inhibition of telomerase in vivo using acyclic nucleoside analogs (also referred to herein as inhibitors or antagonists of telomerase) is therapeutically beneficial. Further, prior to this disclosure, there was no consensus by those in the art that one could predict that such manipulations would have therapeutic utility.

As telomeres are involved in controlling the cell cycle, cell replication and aging, nucleoside analog containing compositions of the present invention can prevent or control uncontrolled cell growth and the immortality of tumor cells. The compositions of the present invention find particular utility in the treatment of cell proliferative disorders, and in particular human tumors characterized as having telomeres maintained by telomerase.

Thus, in an aspect, the present invention features a method for treatment of a condition associated with telomerase, particularly elevated level of telomerase activity in a cell. The method involves administering to that cell or a mammal in need of the treatment a composition containing a therapeutically effective amount of at least one nucleoside analog that is an acyclic, antitelomerase and antineoplastic agent. The level of telomerase activity can be measured as described below, or by any other existing method or equivalent method. By "elevated level" of telomerase activity, it is meant that the absolute level of telomerase activity in the particular cell is elevated compared to normal cells in that subject or individual, or compared to normal cells in other subjects or individuals not suffering from the condition. Examples of such conditions include cancerous conditions, or conditions associated with the presence of cells which are not normally present in that individual. In one embodiment, the compositions contain nucleoside analogs other than AZT, ddI, ddA, d4T (Strahl C, Blackburn E H Effects of reverse transcriptase inhibitors on telomere length and telomerase activity in two immortalized human cell lines. *Mol Cell Biol.* 1996; 16(1): 53-65). Preferably, the compositions contain GCV or ACV or their prodrugs. In another embodiment, these compositions may contain, in addition, clinically acceptable levels of AZT.

The utilization of these telomerase inhibitors (which either directly inhibit the telomerase activity or indirectly incorporate into telomere and thus prevent telomere's further elongation) will lead to progressive telomere shortening in tumors where telomerase is active. Once the telomere length shortens to a critical length, the tumor will go into crisis and eventually die. These telomerase inhibitors should have little or no effect on the normal somatic cells because telomerase activity in normal cells is generally low or undetectable.

Interference with telomerase activity may either directly result in cell death or may potentiate the effects of chemotherapeutic agents that ultimately kill cells through apoptosis. In particular, the invention provides a method for inhibiting proliferation of telomerase expressing cells having potential for continuous increase in cell number by administering the inhibitors and antagonists of telomerase. Administration of a nucleoside analog can be achieved by any desired means well known to those of ordinary skill in the art.

In an embodiment of the invention, a method for prevention of a cancer characterized by expression of telomerase in a mammal or a subject (e.g. a human) in need thereof is provided. The preventive method involves administration of a therapeutically effective amount of a composition to the mammal. The composition has a telomerase inhibitor or antagonist of the present invention. The inhibitor or antagonist blocks the lengthening of telomeres in telomerase-positive cells, thereby inhibiting proliferation of telomerase expressing cells. The inhibitor is an acyclic nucleoside analog or a pharmaceutically acceptable salt of such an analog or a liquid or solid food material that is enriched with the inhibitor or antagonist. The food product can be, for example, a functional food in the form of butter, margarine, biscuits, bread, cake, candy, confectionery, yogurt or another fermented milk product, or cereal suitable for consumption by humans. Alternatively, it can be a nutritional supplement, a nutrient, a pharmaceutical, food, a nutraceutical, a health food and/or a designer food. Periodically, the human is tested for the presence of telomerase positive cells. The use of inhibitor or antagonist may be stopped once the telomerase positive cells are no longer detected in the mammal.

In addition to the therapeutic aspect, the present invention also provides diagnostic methods and kits for detecting pathologically proliferating cells expressing telomerase. These and other embodiments of the invention will be described in more detail below.

DETAILED DESCRIPTION OF THE INVENTION

Figure 1:
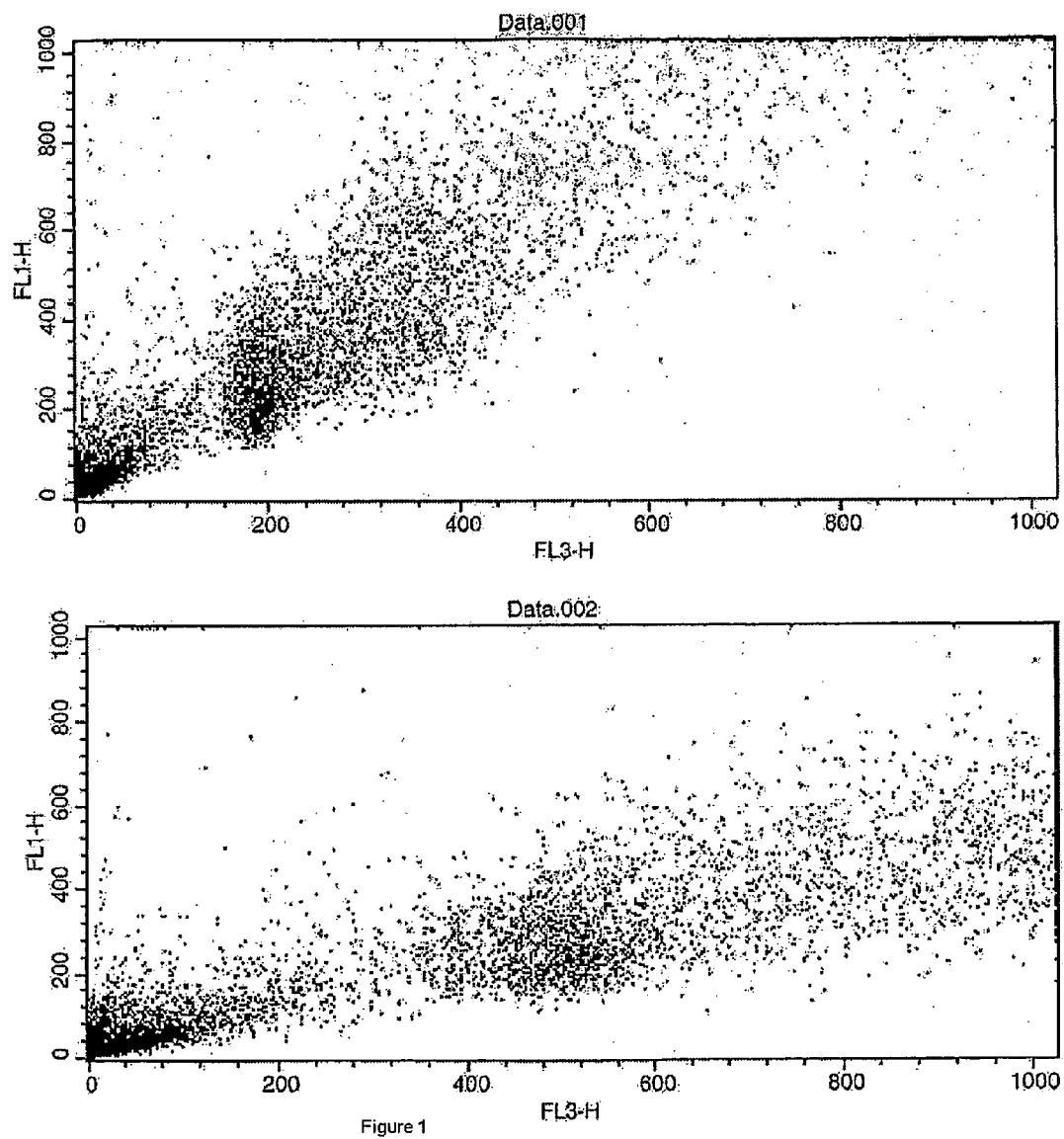
FIG. 1 illustrates flow cytometry data showing decrease in telomere length, massive apoptosis and changes in cell cycle after 10 days of treatment of telomerase positive HeLa cell line with 1.5 µM of GCV. Untreated cells—top panel, treated cells—bottom panel.

The present invention provides compositions and methods involving the use of nucleoside analogs capable of interfering with mammalian telomerase activity. In particular, it has been found that certain nucleoside analogs can affect telomere/telomerase function in cells at clinically acceptable levels. Specifically, in the context of this invention, the "nucleoside analogs" are compounds with structural similarities to the naturally occurring nucleosides but are limited to those analogs that are acyclic. The acyclic nucleoside analogs contemplated in the present invention are those having a purine (or a pyrimidine) skeleton with a tail portion (e.g., 9-(1,3-dihydroxy-2-propoxymethyl present in guanine) but lacking the hydroxyl cyclic ring (pentose). Examples of the analogs of the present invention include but are not limited to the following: acyclovir, ganciclovir, penciclovir and the corresponding pro-drugs, i.e., valacyclovir, valganciclovir and famciclovir, respectively. Acyclovir[12] acts by mimicking a cellular DNA constituent, guanine. That is the "G" in the AT-CG of DNA. Acyclovir (9-[2(hydromethoxy)-methyl] guanine), although structurally similar to "G," is missing its tail—a hydroxyl "cyclic" ring (pentose) and thus it is "acyclic." Ganciclovir[13,14,15] and penciclovir[16,17] are also "acyclic" because they lack the hydroxyl cyclic ring. In an embodiment of the invention, the tail portion of the acyclic nucleoside analogs of the present invention has at least one hydroxyl group mimicking the 3'- and 5'-hydroxyl groups of the 2'-deoxyribose moiety of nucleosides. The acyclic nucleoside analogs of the present invention have been found to exhibit antitelomerase and antineoplastic properties with clinically acceptable degree of toxicity. The acyclic nucleoside analogs acyclovir, ganciclovir, penciclovir and the corresponding pro-drugs, i.e., valacyclovir, valganciclovir and famciclovir, are all approved for clinical use as antiviral drugs. Their chemical structures and dosage regimens for combating viral infections are well known to one skilled in the art.

While acyclovir, ganciclovir, penciclovir and the corresponding pro-drugs are well known as antiviral medicines for the treatment of Herpes virus or/and CMV infections, their use in therapy of neoplastic diseases is unknown. It is also known in the art that the target enzyme for these anti-herpes virus agents is the DNA polymerase.

In the present invention it has been shown that the acyclic antiviral agents can also target eukaryotic telomerase in proliferating cells and tumors. It is believed that these agents, once inside a proliferating cell, get phosphorylated (e.g., di- and triphosphate) forms and compete with the natural substrates (e.g., dGTP) of the telomerase reaction. The phosphorylated analogs can inhibit the incorporation of the natural substrates into the growing telomere DNA chain or can themselves become incorporated into DNA thereby interfering with telomerase mediated polymerization activity, which eventually leads to termination of chain elongation. In essence, these nucleoside analogs, by termination of chain elongation, damage telomeric DNA, shorten telomeres and cause apoptosis.

Damage to telomeres is more detrimental to rapidly growing (e.g., tumor) cells than to normal cells.

The anti-HIV and anti-herpes nucleoside analogs have been reported to be active only after their phosphorylation from the nucleoside to the nucleotide stage. Thus, phosphorylation appears to be a crucial factor for the activity of nucleoside analogs against their targets. In this regard, AZT has been reported to require three consecutive phosphorylations for it to be active against telomerase.

The acyclic nucleoside analogs of the present invention are more potent and selective antitelomerase agents than the prior art known antitelomerase nucleoside analogs such as AZT;

clinically acceptable doses[18, 19, 20, 21, 22] are sufficient for realizing antitelomerase activity and apoptosis or cell death as compared to the nucleoside analogs such as AZT.

Induction of telomere shortening, $G_2$/M arrest (also referred to herein as $G_2$ arrest) and apoptosis in telomerase positive cancer cells after ganciclovir (GCV) and acyclovir (ACV) treatments has been carried out as described below.

To detect telomerase specific activity in two cell lines (Hela and NuTu-19) real time TRAP assay was performed. The reported telomerase-positive cell lines (HeLa) was used for comparison.[4] Both cell lines were positive in this test (data not shown).

Figure 2:
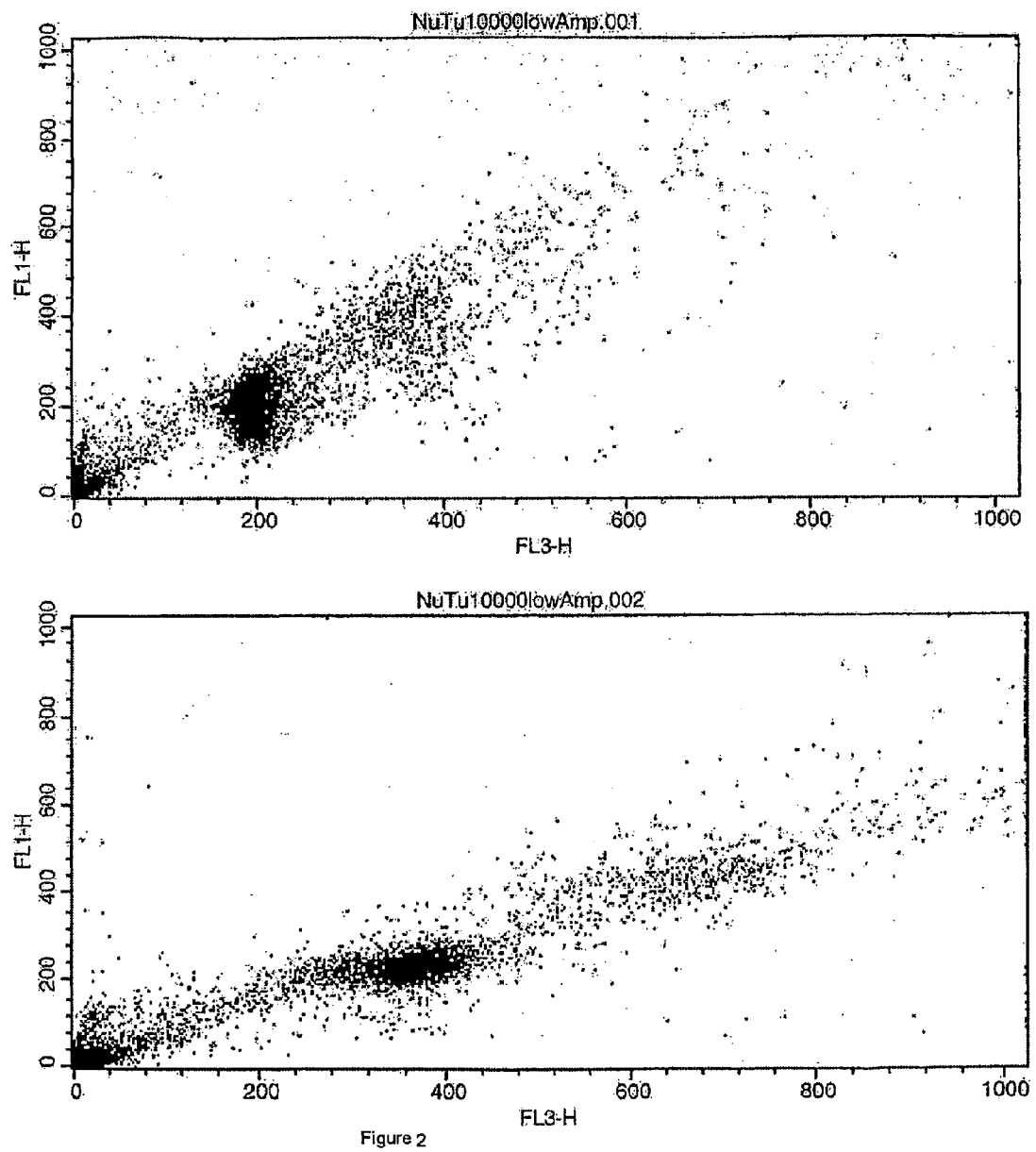
FIG. 2 illustrates flow cytometry data showing decrease in telomere length, massive apoptosis and changes in cell cycle after 14 days of treatment of telomerase positive NuTu-19 cell line with 3 µM of ACV. Untreated cells—top panel, treated cells—bottom panel.

The telomerase positive cell lines were treated with therapeutic concentrations of GCV (1.5 µM) or ACV (3.0 µM), to demonstrate that telomeric DNA synthesis could be inhibited within the cells, and thereby induce telomere shortening. Telomere length in GCV and ACV treated and untreated cell lines was measured by flow cytometry with a telomere- specific peptide nucleic acid (PNA) probe[23, 24]. To determine cell cycle distribution, cells were stained with propidium iodide (PI)[23]. After 14 days of both kinds of treatment, both cell lines demonstrated telomere shortening, massive apoptosis and G2 arrest (FIGS. 1 and 2).

Figure 3:
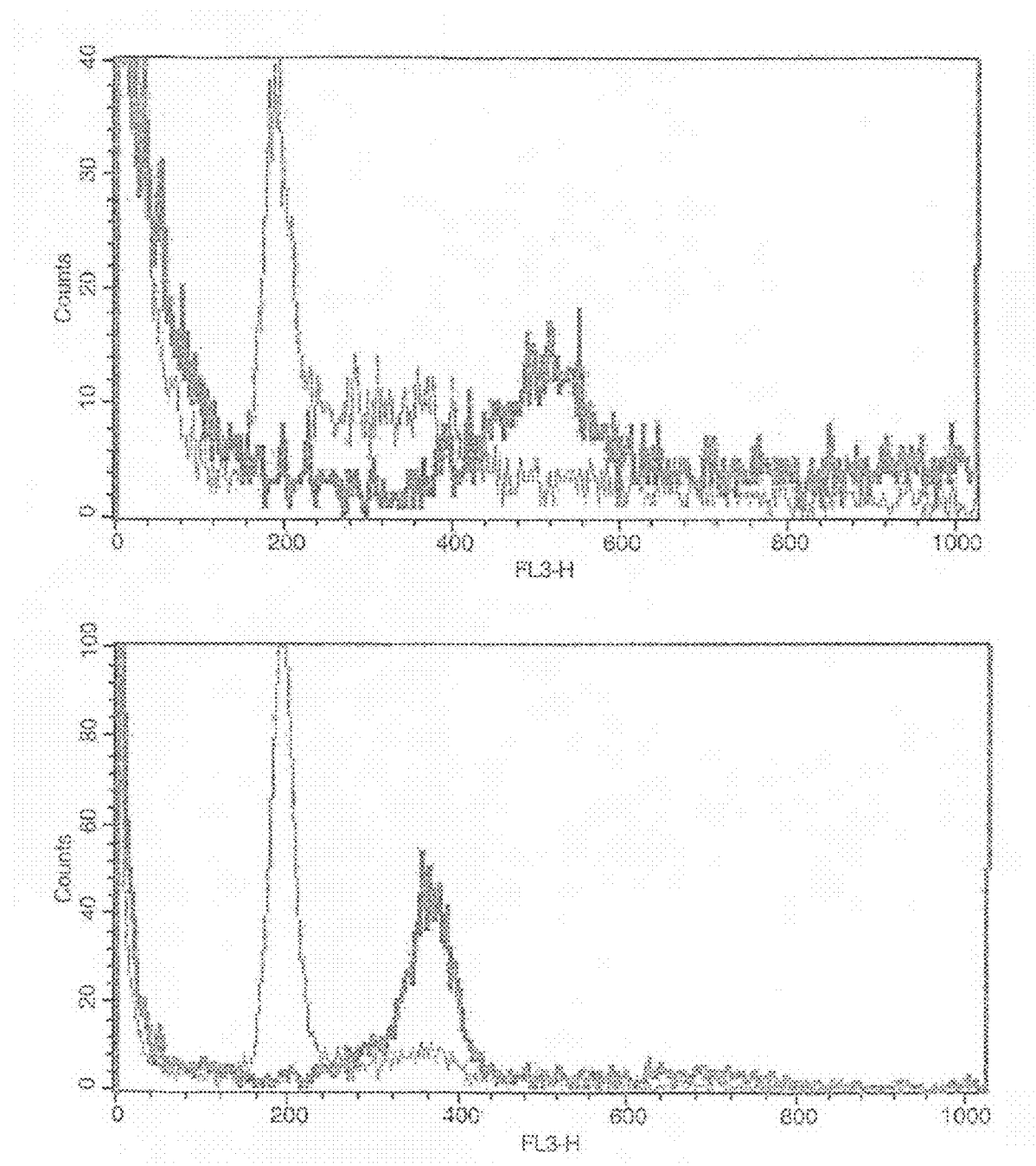
FIG. 3 illustrates flow cytometry data showing changes in the cell cycle distribution in HeLa (top panel) and NuTu-19 (bottom panel) cells treated with 1.5 µM of GCV for 10 days. Untreated cells—grey, treated cells—dark.

To demonstrate changes in cell cycle distribution HeLa and NuTu-19 cells were treated with GCV or ACV for 14 days stained with PI, and analyzed by flow cytometry simultaneously. Results show G2 arrest of cell cycle (FIG. 3). It is important to note that changes were rapid and could be detected after only 14 days of ACV treatment. In contrast, the nucleoside analog, AZT had no effect on telomere length or cell cycle distribution in telomerase positive cells, HeLa and NuTu-19, even at elevated concentrations e.g., 100 µM (data not shown).

At the same time, PI staining demonstrated a higher DNA content in GCV or ACV treated cells at later stages of treatment, compared to untreated cells. A rational explanation of this fact is a short telomere induced chromosome end-to-end joining[25].

The origin of the cell lines are uterine cervix (HeLa) and epithelial ovarian (NuTu-19). Cells were cultured in D-MEM media supplemented with 10% fetal calf serum at 37° C. in a humidified atmosphere of 5% $CO_2$. For treatment of the cells with GCV, the media was supplemented with 1.5 µM of GCV (Cymevene, Hoffman-La Roche). For treatment of the cells with ACV, the media was supplemented with 3 µM of Aciclovir (Aciclovir, TEVA Pharm. Ind. Ltd, Israel).

Real time TRAP assay was performed as described (Wege et al., SYBR Green real-time telomeric repeat amplification protocol for the rapid quantification of telomerase activity. *Nucleic Acids Res.* 2003; 31(2):E3-3).

For telomere length measurement by flow cytometry, cells were stained with telomere specific FITC conjugated $(C_3TA_2)_3$ PNA (Applied Biosystems) probe and contrastained with 0.06 µg/ml PI as described by Rufer, N., Dragowska, W., Thornbury G., Roosnek, B., Lansdorp P. M. Telomere length dynamics in human lymphocyte subpopulations were measured by flow cytometry. *Nat. Biotechnol.* 16, 743-747 (1998)).

Thus, it has been demonstrated herein that the nucleoside analogs GCV and ACV clearly block telomerase positive cancer in widely accepted model systems. Useful telomerase-inhibitory compounds are not believed to be limited in any way to the specific compounds or nucleotide analogs and derivatives specifically exemplified above. In fact, it may prove to be the case that the most useful pharmacological compounds designed and synthesized in light of this disclosure will be second generation derivatives or further-chemically-modified acyclic nucleoside analogs.

Although not suggesting the advantageous uses made possible by this invention, the previous administration of GCV for treating CMV (cytomegalovirus) infections in patients with AIDS or other immunodeficiencies means that GCV can be readily administered to cancer patients.

Further, the present use of a number of acyclic nucleoside analogs to HSV and CMV patients, coupled with the ability to use significantly lower doses of these analogs, should speed up regulatory approval for the use of acyclovir, ganciclovir, penciclovir and the corresponding pro-drugs, i.e., valacyclovir, valganciclovir and famciclovir, in the treatment of telomerase induced and/or mediated cancers.

The present invention also encompasses the use of various animal models. By developing or isolating cell lines that express telomerase one can generate disease models in various laboratory animals. These models may employ the subcutaneous, orthotopic or systemic administration of cells to mimic various disease states. For example, the HeLa cell line can be injected subcutaneously into nude mice to obtain telomerase positive tumors. The resulting tumors should show telomerase activity in telomeric repeat amplification protocol (TRAP) assay. Such animal models provide a useful vehicle for testing the nucleoside analogs individually and in combinations as well.

Determining the effectiveness of a compound in vivo may involve a variety of different criteria including, but are not limited to, survival, tumor regression, arrest or slowing of tumor progression, elimination of tumors and inhibition or prevention of metastasis.

Treatment of animals with a test compound would involve the administration of the compound or composition in an appropriate form to the animal. The pharmaceutical compositions, inhibitory or antagonistic agents of the present invention can be administered in a variety of ways including but not limited to oral, parenteral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

The compositions of the present invention would be important in a number of aspects. They would be important in regimens for the treatment of telomerase-related cancers, whether administered alone or in combination with chemo- and/or radiotherapeutic regimens known to one skilled in the art in the treatment of cancer. Alternatively, by simply reducing telomerase activity, these compositions will be instrumental in selectively inducing massive apoptosis of cancer cells.

The nucleoside analogs may be administered in a physiologically or pharmaceutically acceptable carrier to a host for treatment of proliferative diseases, etc. Pharmaceutically acceptable carriers are determined in part by the particular composition being administered as well as by the particular method used to administer the composition.

In an aspect of the present invention, methods for preventing or treating disorders caused by the presence of inappropriately or pathologically proliferating cells or immortal cells in mammals are provided. The inappropriately or pathologically proliferating cells or immortal cells exist and reproduce independently of cells' normal regulatory mechanisms. These cells are pathologic because they deviate from normal cells as a result of activity of a cellular element, i.e., telomerase. Of course, the term "inappropriately proliferating cells" as used herein may be benign hyperproliferating cells but unless stated otherwise these cells refer to malignant hyperproliferating cells characteristic of a wide variety of tumors and cancers.

In particular, methods for preventing or treating human tumors characterized as expressing telomerase are provided. The human tumors include stomach cancers, osteosarcoma, lung cancers, pancreatic cancers, adrenocortical carcinoma or melanoma, adipose cancers, breast cancers, ovarian cancers, cervical cancers, skin cancers, connective tissue cancers, uterine cancers, anogenital cancers, central nervous system cancers, retinal cancer, blood and lymphoid cancers, kidney cancers, bladder cancers, colon cancers and prostate cancers. The prevention or treatment of the disorders, according to the present invention, is achieved by the utilization of acyclic nucleoside analogs (inhibitors or antagonists of telomerase) of the present invention. The inhibitor(s) or antagonist(s) used in the present invention are those that directly or indirectly interact with telomerase to inhibit its activity and/or those that get incorporated into telomere and thus prevent telomere from further elongation despite the functional telomerase thereby inhibiting the growth of cells expressing telomerase. Thus, the inhibitors or antagonists of telomerase are used for inhibiting the growth of cells. For example, when the inhibitors or antagonists of telomerase are administered to a patient, these cause progressive telomere shortening, cell cycle arrest in the cells and/or massive apoptosis of the cells expressing telomerase. In the present invention, the terms "inhibiting the growth" or "inhibition of growth" may also mean reducing or preventing cell division. Inhibition of growth of cells expressing telomerase, in the present invention, may be about 100% or less but not 0%. For example, the inhibition may be from about 10% to about 100%, preferably at least about 25%, and more preferably at least about 50%, still more preferably at least about 90%, 95% or exactly 100% compared to that of the control cells (control cells express telomerase but are not treated with an inhibitor or antagonist). The inhibition of growth can be measured by any methods known in the art. For example, viable cell number in treated samples can be compared with viable cell number in control samples, determined after incubation with vital stains. In addition, growth inhibition can be measured by assays that can detect reductions in cell proliferation in vitro or in vivo, such as tritiated hydrogen incorporation assays, BdU incorporation assay, MTT assay, changes in ability to form foci, anchorage dependence or losing immortalization, losing tumor specific markers, and/or inability to form or suppress tumors when injected into animal hosts (Dorafshar et al., 2003, J Surg Res., 114:179-186; Yang et al., 2004, Acta Pharmacol Sin., 25:68-75).

The development of a cancerous tumor from a single immortalized cell or few such cells may take several months to years in humans. By practising the present invention, however, cancer can be prevented because the tumorigenic telomerase positive cells treated with telomerase inhibitors lose their proliferative potential before they have had a chance to grow into a tumor. Further, periodic preventative administration of telomerase inhibitors or antagonists to at risk groups in order to stop tumor progression before clinical manifestation of cancer could potentially decrease the rate of new cancer cases significantly.

The nucleoside compounds may be administered either singly or in combinations of different analogs and by any routes of administration, including oral administration. The nucleoside analogs ACV, GCV or their L-valil esters valganciclovir (V-GCV) and valacyclovir (V-ACV) are the preferred nucleoside analogs. All of them are commercially available and the formulations are described in a number of patents and publications.

The cells with telomerase activity should be selectively targeted because these cells depend on telomerase for elongating or maintaining telomeres and the elongation or maintenance of telomeres requires the interaction of the nucleosides and/or their analogs with telomerase. To the extent any specific targeting agent is desired for delivering the analogs to exert anti-cancer effects, the use of targeted ACV or GCV and/or other analogs are contemplated herein. Accordingly, in some embodiments, pharmaceutical compositions may have the active compound, in this case, ACV and GCV or a other nucleoside analog, which has been conjugated to a targeting agent (e.g., a peptide) for specific delivery to particular target cells or to nuclear portion within cells.

The dose of a given inhibitor or antagonist of telomerase can be determined by one of ordinary skill in the art upon conducting routine experiments. Prior to administration to patients, the efficacy may be shown in standard experimental animal models. In this regard any animal model for telomerase induced cancer known in the art can be used (Hahn et al., 1999, Nature Medicine, 5(10):1164-1170; Yeager et al., 1999, Cancer Research, 59(17):4175-4179). The subject, or patient, to be treated using the methods of the invention is preferably human, and can be a fetus, child, or adult. Other mammals that may be treated can be mice, rats, rabbits, monkeys and pigs.

The inhibitors or antagonists can be used alone or in combination with other chemotherapeutics (i.e., non-nucleoside analog based anti-cancer agents) including irradiation. For example, therapy of telomerase induced cancers may be combined with chemo and/or radiotherapy to treat cancers induced by telomerase or some other factors. Examples of chemotherapeutic agents known to one skilled in the art include, but are not limited to, anticancer drugs such as bleomycin, mitomycin, nitrogen mustard, chlorambucil, 5-fluorouracil (5-FU), floxuridine (5-FUdR), methotrexate (MTX), colchicine and diethylstilbestrol (DES). To practice combined therapy, one would simply administer to an animal an inhibitor component of the present invention in combination with another anti-cancer agent (chemo or radiation) in a manner effective to result in their combined anti-cancer actions within the animal or patient. The agents would therefore be provided in amounts effective and for periods of time effective to result in their combined presence in the region of target cells. To achieve this goal, the agents may be administered simultaneously, and in the case of chemotherapeutic agents, either in a single composition or as two distinct compositions using different administration routes. Alternatively, the two treatments may precede, or follow, each other by, e.g., intervals ranging from minutes to hours or days. By way of example, and not limitation, the average daily doses of GCV for systemic use may be 100 mg/kg per day for human adults, 50 mg/kg per day for mice and human infants.

Some variation in dosage may occur depending on the condition of the subject being treated. The physician responsible for administration will be able to determine the appropriate dose for the individual patient and may depend on multiple factors, such as, the age, condition, file history, etc., of the patient in question.

Accordingly, the methods of the invention can be used in therapeutic applications for conditions and diseases associated with telomerase induced pathological proliferation of cells. Diseases that would benefit from the therapeutic applications of this invention include all diseases characterized by cell hyperproliferation including, for example, solid tumors and leukemias, and non-cancer conditions. It is further contemplated that the method of the invention can be used to inhibit the growth of cancer cells not only in an in vivo context but also in an ex vivo situation. The method of the invention is particularly useful for inhibiting the growth of pathologically proliferating human cells ex vivo, including, but not limited to, human cancer cells—osteosarcoma, breast carcinoma, ovarian carcinoma, lung carcinoma, adrenocortical carcinoma or melanoma. Bone marrow purging, which is well known in cancer therapy area, is an example of ex vivo treatment for inhibiting the growth of pathologically proliferating human cells.

The present invention provides methods and kits for identifying inappropriately, pathologically or abnormally proliferating cells due to the expression of telomerase in the cells. The methods can be used as a screening method that aids in diagnosing the presence of a cancerous cell or tumor in a patient by determining the presence (and/or level) of expression of telomerase in tissue from the patient, the presence of telomerase expression being indicative of cancer cells or pathological cell proliferation in the patient.

For example, cancerous tumor samples can be diagnosed by their inability to proliferate in the presence of the acylic nucleoside analogs of the present invention. The diagnosis may further involve the detection of telomerase specific mRNA expression measured by a variety of methods including, but not limited to, hybridization using nucleic acid, Northern blotting, in situ hybridization, RNA microarrays, RNA protection assay, RT-PCR, real time RT-PCR, or the presence of telomerase catalytic subunit encoded protein measured by variety of methods including, but not limited to, Western blotting, immunoprecipitation or immunohistochemistry, or enzymatic activity of telomerase (TRAP assay and its modifications[4, 26, 27]).

In a preferred embodiment, nucleic acid probes directed against telomerase catalytic subunit RNA can be used to detect presence and/or increases in telomerase catalytic subunit RNA mRNA levels in tissues undergoing rapid proliferation, such as primary cancer cells, including human osteosarcoma, breast carcinoma, ovarian carcinoma, lung carcinoma, adrenocortical carcinoma or melanoma. Thus, the present invention provides methods of using nucleic acid probes that are complementary to a subsequence of an telomerase to detect and identify pathologically proliferating cells, including cancer cells. For example, the method for identifying a pathologically proliferating cell may involve using a nucleic acid probe directed against an hTERT mRNA to compare the level of expression of hTERT mRNA in a test cell with the level of expression of hTERT mRNA in a control cell. A test cell is identified as a pathologically proliferating cell when the level of hTERT expression is observed as in the control cell. The nucleic acid probe used in the method of the invention, however, may also be substantially complementary to an hTERT MRNA sequence of human mouse or other mammal.

It will be apparent to one of ordinary skill in the art that substitutions may be made in the nucleic acid probe which will not affect the ability of the probe to effectively detect the hTERT mRNA in pathologically proliferating cells (e.g., cancer cells) and thus, such substitutions are within the scope of the present invention. The nucleic acid probe used in the method of the present invention can be a DNA probe, or a modified probe such a peptide nucleic acid probe, a phosphorothioate probe, or a 2'-O methyl probe. The length of the nucleic acid probe may be from about 8 or 10 to 50 nucleotides, preferably from about 15 to 25 nucleotides in length.

The method of the invention can be readily performed in a cell extract, cultured cell, or tissue sample from a human, a mammal, or other vertebrate.

The methods of the present invention are useful for detecting the inappropriately, pathologically or abnormally proliferating cells due to the expression of telomerase in the cells in vitro, in cell cultures, and in human cells and tissues, such as solid tumors and cancers (e.g., human osteosarcoma, breast carcinoma, ovarian carcinoma, lung carcinoma, adrenocortical carcinoma or melanoma).

The present invention also provides kits for detecting and/or inhibiting hyperproliferating cells or cancer cells. The kit can have ACV, GCV, valganciclovir valaciclovir or other acyclic nucleoside analogs and/or have a nucleic acid probe that is fully or substantially complementary to a subsequence of an hTERT mRNA.

The pharmaceutical compositions, inhibitory or antagonistic agents of the present invention can be administered in a variety of ways including orally, topically, parenterally e.g. subcutaneously, intraperitoneally, by viral infection, intravascularly, etc. Depending upon the manner of introduction, the compounds may be formulated in a variety of ways. Formulations suitable for oral administration can be liquid solutions. Formulations suitable for parenteral administration (e.g., by intraarticular, intraventricular, intranasal, intravenous, intramuscular, intradermal, intraperitoneal, and subcutaneous routes) include aqueous and non-aqueous, isotonic sterile injection solutions. In the practice of this invention, compositions can be administered, for example, by intravenous infusion, orally, topically, parenterally or intraperitoneally. Oral and parenteral administrations are the preferred methods of administration. Techniques for formulation and administration are routine in the art and further details may be found, for example, in Remington's Pharmaceutical Sciences (2000), Gennaro AR(ed), 20th edition, Maack Publishing Company, Easton, Pa.

Therapeutically effective amount (or effective amount) or pharmacologically effective amount are well recognized phrases in the art and refer to that amount of an agent effective to produce the intended pharmacological result. For example, a therapeutically effective amount is an amount sufficient to effect a beneficial therapeutic response in the patient over time (i.e., to treat a disease or condition or ameliorate the symptoms of the disease being treated in the patient). Therapeutically effective amount of acyclic nucleoside analog(s) (or a composition thereof) is that amount effective to reproducibly induce telomere shortening, $G_2$ arrest and/or massive apoptosis in cancer cells in an assay in comparison to levels in untreated cells. Therapeutically effective amount of acyclic nucleoside analog(s) (or a composition thereof) also means an amount of acyclic nucleoside analog(s) that will decrease, reduce, inhibit or otherwise abrogate the growth of cancer cells. The amount will preferably be an optimized amount such that the desired effect is achieved without significant side effects. As described further in detail below, the dose may also be determined by the efficacy of the particular inhibitor or antagonistic agent employed and the condition of the patient, as well as the body weight or surface area of the patient to be treated. The size of the dose also will be determined by the existence, nature, and extent of any adverse side-effects that accompany the administration of, for example, a particular agent, vector or transduced cell type to a particular patient.

Therapeutically effective doses of agent(s) capable of preventing, inhibiting or reducing the incidence of telomerase mediated cancer are readily determinable using data from cell culture assays disclosed herein and/or from in vivo assays using an animal model. The animal model can also be used to estimate appropriate dosage ranges and routes of administration in humans. Experimental animals bearing solid tumors of human origin (or art-accepted animal models) are frequently used to optimize appropriate therapeutic doses prior to translating to a clinical environment. Such models are known to be very reliable in predicting effective anti-cancer strategies. For example, mice bearing solid tumors are art-accepted mouse models and are widely used in pre-clinical testing to determine working ranges of therapeutic agents that give beneficial anti-tumor effects with minimal toxicity. Due to the safety already demonstrated in art-accepted models, at least with respect to nucleoside analogs used in the context of telomerase-mediated cancer, pre-clinical testing of the present invention will be more of a matter of routine experimentation. In vivo efficacy may be predicted using assays that measure inhibition of tumor formation (progression), tumor regression or metastasis, and the like.

Exemplary in vivo assays of anti-tumor efficacy of ACV and/or GCV using nude mice subcutaneous (s.c.) tumors grown from the human HeLa cancer cell line (i.e., xenografts bearing mice) as cancer models are described below.

Human cancerous cells needed for in vivo assays may be prepared, for example, as follows: Telomerase positive HeLa human cell line can be obtained from public sources. Cells are maintained in D-MEM media supplemented with 10% foetal calf serum at 37° C. in a humidified atmosphere of 5% $CO_2$.

For in vivo assay, appropriate host, e.g., nude (nu/nu) mice of about 5-7 weeks old are obtained and maintained in pathogen-free conditions. Approximately, $1 \times 10^6$ HeLa cells contained in 200 μl of serum-free media are delivered to all animals, briefly anaesthetized with Metofane, by subcutaneous (s.c.) injection in flank. Then the mice are divided into experimental group and control group.

In one embodiment, impairment of s.c. tumor growth or time to progression rather than decrease in size of an established tumor is assessed. In this embodiment, starting from the day zero, mice in the experimental group receive GCV in drinking water ad libitum. Concentration of GCV in water can be 2 mg/ml. Fresh solution of GCV is supplied every 3 days. Mice in the control group receive only drinking water. Tumors are measured every 2-3 days. Mice are sacrificed when tumors exceed 1 cm³. Tumor volume is calculated with formula $4/3\pi r^3$, where r is the radius of the tumor. All mice in the control group should develop tumors and all mice in the experimental group remain tumor free.

An in vivo was carried out as follows: Nude mice were injected s.c. with HeLa cells ($3 \times 10^5$) to demonstrate prevention of development and treatment of telomerase positive tumors in vivo. Human cancer HeLa cell culture was purchased from ATCC. In all, 12 CD1/-nu and 12 NMRiI/-nu nude mice were purchased from Charles River Laboratories, Charles River Deutschland GmbH. These nude mice were injected s.c. with 3×105 HeLa cells. Experimental group received valganciclovir in drinking water from day 0. Specifically, mice in the experimental groups (6 mice per strain) were exposed to Valcyte (val-ganciclovir) in drinking water (1 mg/ml) from day 0. All mice in control and treated groups had developed tumors. In about 14 days, all mice were bearing the tumors. The tumor in one mouse from the treated group began to regress and, by about the 30th day, this tumor was eliminated by monotherapy with Valcyte. Other mice in the treated groups demonstrated slowing of tumor growth (stabilization).

In another embodiment, the reagents and methods of the invention can be used to promote tumor regression in vivo in immunocompetent animals carrying pre-established tumors; i.e., the reagents of the invention can be used to treat animals with pre-existing tumors. In this case, the cancerous $10^6$ NuTu-19 cells are injected subcutaneously in the flank of the Fischer rats to establish tumors. Once tumors are established after tumor cell implantation, the rats in the experimental group are administered with a composition containing GCV (or ACV) i.g. solution in drinking water ad libitum, and the rats in the control group receive the same composition but without the drug (e.g., distilled water Tumor growth is monitored every 2-3 days. When GCV (or ACV) is administered 21-28 days to these tumor bearing animals, retarded tumor growth is observed. Such inhibition of tumor cell growth is not observed in the control group. Few weeks after the start of the treatment, only the animals treated with GCV show 100% survival.

In another embodiment, in vivo assays that qualify the promotion of apoptosis may also be used. In this embodiment, xenograft bearing animals treated with the therapeutic composition may be examined for the presence of apoptotic foci and compared to untreated control xenograft-bearing animals. The extent to which apoptotic foci are found in the tumors of the treated animals provides an indication of the therapeutic efficacy of the composition.

From the above exemplary in vivo assays, it should be apparent that the combination treatment that uses non-nucleoside analog based anti-cancer agents (such as, for example, bleomycin, mitomycin, nitrogen mustard, chlorambucil, 5-fluorouracil (5-FU), etc., listed above) or irradiation is not a requirement of the invention. The use of acyclic nucleoside analog(s) alone or in combination with nucleoside analogs that are not acyclic is sufficient to induce telomere shortening, $G_2$ arrest and/or massive apoptosis in cancer cells and thus is sufficient to achieve more than a mere weak growth delay of tumors (or sufficient to dramatically reduce the growth delay of tumors). Accordingly, in some aspects, the present invention does not involve the use of non-nucleoside analog based anti-cancer agents or irradiation. Also, in some aspects of the present invention (methods of treatment or prevention of tumor growth), the following nucleoside analogs are excluded or not used: HPMPC [(S)-1-[3-hydroxy-2-(phosphomethoxy)propyl]cytosine]; HPMPA which is an adenine derivative or 9-(2-[phosphonylmethoxyethyl]) (PMEA, adefovir), which are derivatives of adenine, or guanine (PMEG), 2-6 diaminopurine (PMEDAP), cyclo-propyl PMEDAP (cPr-PMEDAP).

This invention encompasses the use of telomerase inhibitors-based cancer therapy for a wide variety of tumors and cancers affecting skin, connective tissues, adipose, breast, lung small cell lung carcinomas and non-small cell lung cancer (NSCLC)), stomach (gastric cancer), pancreas, ovary, cervix, uterus, kidney, bladder, colon, prostate, anogenital, central nervous system (CNS), retina and blood and lymph (lymphomas resulting from the expression of CDK9/CYCLIN T1 in precursor T cells, precursor B cells, germinal center cells, activated T cells or Reed-Sternberg cells), virus-associated cancers (HBV-associated cancers, EBV-associated cancers HCV-associated cancers and HPV-associated cancers) known in the art, and other cancers mentioned elsewhere in this disclosure. In an aspect, however, the present invention does not include treatment or prevention of virus-associated cancers known in the art.

In designing appropriate doses of agent(s) for the treatment of human telomerase-mediated caners (both early stage tumors and vascularized tumors), one may readily extrapolate from the animal studies described herein in order to arrive at appropriate doses for clinical administration. To achieve this conversion, one would account for the mass of the agents administered per unit mass of the experimental animal and, preferably, account for the differences in the body surface area between the experimental animal and the human patient. All such calculations are well known and routine to those of ordinary skill in the art. Thus, the determination of a therapeutically effective dose is well within the capability of those skilled in the art.

For example, in taking the successful doses of GCV or ACV (V-GCV or V-ACV) in cell culture assays and in the mouse studies, and applying standard calculations based upon mass and surface area, effective doses for use in adult human patients would be between about 1000 mg and about 6000 mgs of GCV or ACV per patient per day, and preferably, between about 500 mgs and about 1000 mgs of V-GCV or V-ACV per patient per day. Accordingly, using this information, it is contemplated herein that low doses of therapeutic agents (e.g., acyclovir, ganciclovir, penciclovir and the corresponding pro-drugs, i.e., valacyclovir, valganciclovir and famciclovir) for human administration may be about 1, 5, 10, 20, 25 or about 30 mgs or so per patient per day; and useful high doses of therapeutic agent for human administration may be about 250, 300, 400, 450, 500 or about 600 mgs or so per patient per day. Useful intermediate doses may be in the range from about 40 to about 200 mgs or so per patient Notwithstanding these stated ranges, it will be understood that, given the parameters and detailed guidance presented herein, further variations in the active or optimal ranges will be encompassed within the present invention. The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 1-500 mgs, and preferably, between about 10-100 mgs of the inhibitor or antagonist of telomerase or therapeutic cocktail containing such, about −4 times within about a 60 days period. For example, doses would be given on about day 1, day 3 or 4 and day 6 or 7. Administration can be accomplished via single or divided doses taken orally or, for example, by administration to the site of a solid tumor directly or in a slow release formulation. The physician responsible for administration will, in light of the present disclosure, be able to determine the appropriate dose for the individual subject, the form and route of administration. Such optimization and adjustment are routinely carried out in the art and by no means reflect an undue amount of experimentation. In administering the particular doses themselves, one would preferably provide a pharmaceutically acceptable composition according to regulatory standards of sterility, pyrogenicity, purity and general safety to the human patient systemically. Physical examination, tumor measurements, and laboratory tests should, of course, be performed before treatment and at intervals up to one to few months after the treatment and one skilled in the art would know how to conduct such routine procedures. Clinical responses may be defined by any acceptable measure. For example, a complete response may be defined by the disappearance of all measurable tumors within a given period after treatment.

The references numbered 1-27 below are cited in the above description (with the corresponding superscript numbers) and as such one skilled in the art would match the references to the appropriate superscript numbers in the text above.

1. Olovnikov, A. M. Principle of marginotomy in template synthesis of polynucleotides. *Dokl. Akad. Nauk SSSR* 201, 1496-1499 (1971).

2. Allshire, R. C., Dempster, M., Hastie, N. D. Human telomeres contain at least three types of G-rich repeat distributed non-randomly. *Nucleic Acids Res.* 17, 4611-4627 (1989).
3. Greider, C. W., Blackburn, E. H. Identification of a specific telomere terminal transferase activity in Tetrahymena extracts. *Cell* 43, 405-413 (1985).
4. Morin G B. The human telomere terminal transferase enzyme is a ribonucleoprotein that synthesizes TTAGGG repeats. Cell. 1989 Nov. 3; 59(3):521-9.
5. Kim, N. W., Piatyszek, M. A., Prowse, K. R., Harley, C. B., West, M. D. Specific association of human telomerase activity with immortal cells and cancer. *Science* 266, 2011-2015 (1994).
6. Harley, C. B., Futcher, A. B., Greider, C. W. Telomeres shorten during ageing of human fibroblasts. *Nature* 34, 458-460 (1990).
7. Bryan, T. M., Englezou, A., Dalla-Pozza, L., Dunham, M. A., Reddel, R. R. Evidence for an alternative mechanism for maintaining telomere length in human tumors and tumor-derived cell lines. *Nat. Med.* 3, 1271-1274 (1997).
8. Reddel, R. R., Bryan, T. M., Colgin, L. M., Perrem, K. T., Yeager, T. R. Alternative lengthening of telomeres in human cells. *Radiat. Res.* 155, 194-200 (2001).
9 Wright, W. E., Piatyszek, M. A., Rainey, W. E., Byrd, W., Shay, J. W. Telomerase activity in human germline and embryonic tissues and cells. *Dev. Genet.* 18, 173-179 (1996).
10. Greider C W Mammalian telomere dynamics: healing, fragmentation shortening and stabilization. *Curr Opin Genet Dev.* 1994; 4(2):203-11.
11. Hahn, W. C. et al. Inhibition of telomerase limits the growth of human cancer cells. *Nat. Med.* 5, 1164-1170 (1999).
12. Elion, G. B.; Furman, P. A.; Fyfe, J. A.; de Miranda, P.; Beauchamp, L.; Schaeffer, H. J. Selectivity of Action of an Antiherpetic Agent, 9-(2-Hydroxyethoxymethyl)guanine. *Proc. Natl. Acad. Sci. U.S.A.* 1977, 74, 5716-5720.
13. Martin, J. C.; Dvorak, C. A.; Smee, D. F.; Matthews, T. R.; Julien, P. H.; Verheyden, J. P. H. 9-[(1,3-Dihydroxy-2-propyloxy)methyl]guanine: A New Potent and Selective Antiherpes Agent. *J. Med. Chem.* 1983, 26, 759-761.
14. Smee, D. P.; Martin, J. C.; Verheyden, J. P. H.; Matthews, T. R. Antiherpesvirus Activity of the Acyclic Nucleosides 9-(1,3-Dihydroxy-2-propoxymethyl)guanine. *Antimicrob. Agents Chemother.* 1983, 23, 676-682.
15. Field, E. K.; Davies, M. E.; DeWitt, C.; Perry, H. C.; Liou, R.; Germershausen, J.; Karkas, J. D.; Ashton, W. T.; Johnston, D. B.; Tolman, R. L. 9-([2-Hydroxy-1-(hydroxymethyl)ethoxy]methyl)guanine: A Selective Inhibitor of Herpes Group Virus Replication. *Proc. Natl. Acad. Sci. U.S.A.* 1983, 80, 4139-4143.
16. Harnden, M. R.; Jarvest, R. L.; Bacon, T. H.; Boyd, M. R. Synthesis and Antiviral Activity of 9-[4-Hydroxy-3-(hydroxymethyl)but-1-yl]purines. *J. Med. Chem.* 1987, 30, 1636-1643
17. Vere Hodge, R. A.; Perkins, R. M. Mode of Action of 9-(4-Hydroxy-3-hydroxymethylbut-1-yl)guanine (BRL 39123) against Herpes Simplex Virus in MRC-5 Cells. *Antimicrob. Agents Chemother.* 1989, 33, 223-229
18. de Miranda P, Whitley R J, Blum M R, Keeney R E, Barton N, Cocchetto D M, Good S, Hemstreet G P 3rd, Kirk L E, Page D A, Elion G B. Acyclovir kinetics after intravenous infusion. *Clin Pharmacol Ther.* 1979; 26(6):718-28.
19. Van Dyke R B, Connor J D, Wybomy C, Hintz M, Keeney R E. Pharmacokinetics of orally administered acyclovir in patients with herpes progenitalis. *Am J Med.* 1982; 73(1A): 172-5.
20. Lycke J, Malmestrom C, Stahle L. Acyclovir levels in serum and cerebrospinal fluid after oral administration of valacyclovir. Antimicrob Agents Chemother. 2003; 47(8): 2438-41.
21. Piketty C, Bardin C, Gilquin J, Gairard A, Kazatchkine M D, Chast F. Monitoring plasma levels of ganciclovir in AIDS patients receiving oral ganciclovir as maintenance therapy for CMV retinitis. *Clin Microbiol Infect.* 2000; 6(3):117-20.
22. Brown F, Banken L, Saywell K, Arum I. Pharmacokinetics of valganciclovir and ganciclovir following multiple oral dosages of valganciclovir in HIV- and CMV-seropositive volunteers. *Clin Pharmacokinet.* 1999; 37(2):167-76.
23. Rufer, N., Dragowska, W., Thornbury G., Roosnek, E., Lansdorp P. M. Telomere length dynamics in human lymphocyte subpopulations measured by flow cytometry. *Nat. Biotechnol.* 16, 743-747 (1998).
24. Hultdin, M. et a.l Telomere analysis by fluorescence in situ hybridization and flow cytometry. *Nucleic Acids Res.* 26, 3651-3656 (1998).
25. Guiducci, C., Cerone, M. A., Bacchetti, S. Expression of mutant telomerase in immortal telomerase-negative human cells results in cell cycle deregulation, nuclear and chromosomal abnormalities and rapid loss of viability. *Oncogene* 20, 714-725 (2001).
26. TRAP-ELISA A. K. Velin, A. Herder, K. J. Johansson et al., Telomerase is not activated in human hyperplastic and adenomatous parathyroid tissue. *Eur J Endocrinol* 145 (2001), pp. 161-164.
27. real time TRAP (Wege et al., SYBR Green real-time telomeric repeat amplification protocol for the rapid quantification of telomerase activity. *Nucleic Acids Res.* 2003; 31(2):E3-3).

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

What is claimed is:

1. A method for preventing or treating disorders caused by the presence of inappropriately or pathologically proliferating cells or immortal cells or for treating a telomerase positive cancer in a mammal or a human, the method comprising administering a therapeutically effective amount of a composition comprising one or more acyclic nucleoside analogs, or a pharmaceutically acceptable salt thereof, to the human suffering from the cancer, wherein the therapeutically effective amount of said composition is that amount effective to reproducibly induce telomere shortening, $G_2$ arrest and/or massive apoptosis in cancer cells in an assay in comparison to levels in untreated cells, wherein said nucleoside analogs induce telomere shortening in said cells, wherein said nucleoside analogs are selected from the group consisting of: acyclovir and penciclovir, or a prodrug thereof.

2. The method of claim 1, wherein said nucleoside analogs is acyclovir; or a prodrug thereof.

3. The method of claim 1, wherein the cancer is selected from the group consisting of: bone cancer, breast cancer, prostate cancer, liver cancer, pancreatic cancer, lung cancer, brain cancer, ovarian cancer, uterine cancer, testicular cancer, skin cancer, leukemia, melanoma, esophageal cancer, stomach cancer, colon cancer, retinal cancer, or bladder cancer.

4. The method of claim 1, wherein the composition is administered orally, parenterally, subcutaneously, intramuscularly or intravascularly.

5. The method of claim 1, wherein said nucleoside analogs is penciclovir or a prodrug thereof.

6. The method of claim 1, wherein the one of said nucleoside analogs administered is from about 10 mg/kg of body weight to about 150 mg/kg of body weight per day.

7. The method of claim 1, wherein said nucleoside analogs are administered in combination with a different type of analog selected from the group consisting of: 3'-azido-2',3'-dideoxythymidine (AZT), 2',3'-dideoxyinosine (ddI), and 2',3'-didehydro-3'-deoxythymidine (d4T), wherein the different type of analog is present in a low dose, which alone is insufficient to treat cancer.

8. A method of reducing telomeric extension in telomerase positive cancer cells, the method comprising administering to the cells an effective amount of an acyclic nucleoside analog, wherein said nucleoside analog is selected from the group consisting of: acyclovir and penciclovir, or a prodrug thereof, wherein said nucleoside analog induces telomere shortening in said cells.

9. The method of claim 8, wherein said nucleoside analog is acyclovir or a prodrug thereof.

10. The method of claim 9, wherein said nucleoside analog is administered in combination with a different type of analog selected from the group consisting of: 3'-azido-2',3'-dideoxythymidine (AZT), 2',3'-dideoxyinosine (ddI), and 2',3'-didehydro-3'-deoxythymidine (d4T), wherein the different type of analog is present in a low dose, which alone is insufficient to terminate lengthening of telomeres.

11. The method of claim 8, wherein said cancer cells are breast cancer cells, prostate cancer cells, liver cancer cells, bone cancer cell, pancreatic cancer cells, lung cancer cells, brain cancer cells, ovarian cancer cells, uterine cancer cells, testicular cancer cells, skin cancer cells, leukemia cells, esophageal cancer cells, stomach cancer cells, colon cancer cells, retinal cancer cells, or bladder cancer cells or a combination of such cells.

12. A method of preventing or inhibiting the growth of a telomerase positive cell, the method comprising contacting the cell with a sufficient amount of an acyclic nucleoside analog such that induction of telomere shortening, G2 arrest and apoptosis in said cell is achieved, wherein said nucleoside analog is selected from the group consisting of: acyclovir and penciclovir, or a prodrug thereof.

13. The method of claim 12, wherein the cell is contacted with a nucleoside analog at a concentration of from about 1.5μM to 3.0μM.

14. The method of claim 12, wherein the nucleoside analog is acyclovir, or a prodrug thereof.

15. The method of claim 12, wherein the telomerase positive cell is a cancer cell, wherein the cancer cell is selected from the group consisting of osteosarcoma, breast carcinoma, ovarian carcinoma, lung carcinoma, adrenocortical carcinoma and melanoma.

16. A method for prevention of a cancer in a person in need thereof, wherein the cancer is due to telomerase activity in cells of the person, the method comprising administering to said person a therapeutically effective amount of a composition comprising one or more acyclic nucleoside analogs, or a pharmaceutically acceptable salt thereof wherein said nucleoside analogs are selected from the group consisting of: acyclovir and penciclovir, or a prodrug thereof, wherein said nucleoside analogs induce telomere shortening in said cells and impair or prevent tumorigenic telomearse positive cells from having a chance to grow into a cancer.

17. The method according to claim 16, wherein said cancer is selected from the group consisting of: bone cancer, breast cancer, prostate cancer, liver cancer, pancreatic cancer, lung cancer, brain cancer, ovarian cancer, uterine cancer, testicular cancer, skin cancer, leukemia, melanoma, esophageal cancer, stomach cancer, colon cancer, retinal cancer, or bladder cancer.

18. A method of promoting apoptosis in telomerase positive cancer cells comprising administering an effective amount of a composition comprising one or more acyclic nucleoside analogs, or pharmaceutically acceptable salts thereof to said cells, wherein said nucleoside analog are selected from the group consisting of: acyclovir and penciclovir, or a prodrug thereof, wherein said nucleoside analogs induce telomere shortening in said cells.

19. The method of claim 18, wherein said nucleoside analogs induce G2 arrest.

20. The method of claim 19, wherein said cancer cells are breast cancer cells, prostate cancer cells, liver cancer cells, bone cancer cell, pancreatic cancer cells, lung cancer cells, brain cancer cells, ovarian cancer cells, uterine cancer cells, testicular cancer cells, skin cancer cells, leukemia cells, esophageal cancer cells, stomach cancer cells, colon cancer cells, retinal cancer cells, or bladder cancer cells or a combination of such cells.

\* \* \* \* \*